United States Patent
Leying et al.

(10) Patent No.: US 10,100,374 B2
(45) Date of Patent: Oct. 16, 2018

(54) HAV DETECTION

(71) Applicant: Roche Molecular Systems, Inc., Pleasanton, CA (US)

(72) Inventors: Hermann Leying, Rotkreuz (CH); Ning Lu, Pleasanton, CA (US); Nick Newton, Oakland, CA (US); Andreas Wolfelschneider, Rotkreuz (CH); Karen Young, San Ramon, CA (US); Dirk Zimmermann, Zug (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 198 days.

(21) Appl. No.: 14/088,007

(22) Filed: Nov. 22, 2013

(65) Prior Publication Data

US 2014/0170638 A1    Jun. 19, 2014

Related U.S. Application Data

(60) Provisional application No. 61/736,686, filed on Dec. 13, 2012.

(51) Int. Cl.
- *C12Q 1/68* (2018.01)
- *C12P 19/34* (2006.01)
- *C12Q 1/70* (2006.01)

(52) U.S. Cl.
CPC .............. *C12Q 1/706* (2013.01); *Y02A 50/54* (2018.01)

(58) Field of Classification Search
None
See application file for complete search history.

(56) References Cited

U.S. PATENT DOCUMENTS

| | | | | |
|---|---|---|---|---|
| 5,501,963 A | * | 3/1996 | Burckhardt | C12Q 1/686 435/267 |
| 2004/0072150 A1 | * | 4/2004 | Shyamala | 435/5 |
| 2012/0003624 A1 | | 1/2012 | Bosch Navarro et al. | |
| 2012/0219941 A1 | | 8/2012 | Shyamala | |

FOREIGN PATENT DOCUMENTS

| | | |
|---|---|---|
| CN | 1675378 A | 9/2005 |
| CN | 200910041358 A | 3/2010 |
| CN | 200910041358 B | 8/2011 |
| EP | 13162833 | 7/2013 |
| KR | 20020078708 A * | 10/2002 |
| KR | 2009109462 A | 5/2011 |
| WO | 199313226 A1 | 7/1993 |
| WO | 03/106641 A2 | 12/2003 |
| WO | 2003106641 A2 | 12/2003 |
| WO | 2006007603 A2 | 1/2006 |
| WO | 2013036332 A2 | 3/2013 |
| WO | WO 2013036332 A3 * | 5/2013 |

OTHER PUBLICATIONS

Henriques et al., "Prevalence of Parvovirus B19 and Hepatitis A virus in Portuguese blood donors," Transfusions and Apheresis Science, 2005, vol. 33, pp. 305-309.*
Costafreda et al., "Development, Evaluation, and Standardization of a Real-Time TaqMan Reverse Transcription-PCR Assay for Quantification of Hepatitis A Virus in Clinical and Shellfish Samples," Applied and Environmental Microbiology, Jun. 2006, vol. 72, No. 6, pp. 3846-3855.*
"Cobas TaqScreen DPX Test for use on the cobas s 201 system", Doc. Rev. 3.0, Oct. 2012.
Abd-Elsalam, "Bioinformatic tools and guideline for PCR primer design," African Journal of Biotechnology 2:91-95 (2003).
Clontech, "General PCR Guidelines," Web Document Reprint (2015).
Kenneth Goossens, "Engineering of Lipid Metabolism in the Diatom Phaeodactylum tricornutum," Universiteit Gent Faculty of Sciences, Masters Dissertation (2012).
Methods in Molecular Biology, Springer Protocols: RT-PCR Protocols, Second Edition, Edited by Nicola King, Human Press (2010).
Qu, et al., MFEprimer: multiple factor evaluation of the specificity of PCR Primers, Bioinformatics 25(2):276-278 (2009).
Singh and Kumar, "PCR Primer Design," Molecular Biology Today 2(2):27-32 (2001).
Anton Yuryev, "Methods in Molecular Biology: PCR Primer Design," Humana Press (2007).
Xu, et al., "Construction and Primary Application of TaqMan PCR Detection Method for Detection of Hepatitis A Virus RNA," China Preventative Medicine 8(3):229-231 (2007).

* cited by examiner

*Primary Examiner* — Young J Kim
(74) *Attorney, Agent, or Firm* — David J. Chang; Jeffery P. Bernhardt; Olga Kay

(57) ABSTRACT

Methods for detecting HAV in a biological sample are provided, comprising amplifying a target nucleic acid comprising the sequence of HAV in a reaction mixture. The reaction mixture comprises a biological sample which may contain the target nucleic acid and set of oligonucleotides. The invention also provides kits for the detection of HAV.

5 Claims, No Drawings

Specification includes a Sequence Listing.

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence

```
<220> FEATURE:
<223> OTHER INFORMATION: oligo

<400> SEQUENCE: 1
ttgcgccccg cggggtcaac                                               20

<210> SEQ ID NO 2
<211> LENGTH: 19
<212> TYPE: DNA
<213> ORGANISM: Artificial Sequence
<220> FEATURE:
<223> OTHER INFORMATION: oligo

<400> SEQUENCE: 2
ttgcgcccgg cggggtcaa                                                19

<210> SEQ ID NO 3
<211> LENGTH: 17
<212> TYPE: DNA
<213> ORGANISM: Artificial Sequence
<220> FEATURE:
<223> OTHER INFORMATION: oligo

<400> SEQUENCE: 3
cgcccggcgg ggtcaac                                                  17

<210> SEQ ID NO 4
<211> LENGTH: 16
<212> TYPE: DNA
<213> ORGANISM: Artificial Sequence
<220> FEATURE:
<223> OTHER INFORMATION: oligo

<400> SEQUENCE: 4
cgcccggcgg ggtcaa                                                   16

<210> SEQ ID NO 5
<211> LENGTH: 21
<212> TYPE: DNA
<213> ORGANISM: Artificial Sequence
<220> FEATURE:
<223> OTHER INFORMATION: oligo

<400> SEQUENCE: 5
ggctctcccc ttgccctagg c                                             21

<210> SEQ ID NO 6
<211> LENGTH: 18
<212> TYPE: DNA
<213> ORGANISM: Artificial Sequence
<220> FEATURE:
<223> OTHER INFORMATION: oligo

<400> SEQUENCE: 6
ggctctcccc ttgcccta                                                 18

<210> SEQ ID NO 7
<211> LENGTH: 19
<212> TYPE: DNA
<213> ORGANISM: Artificial Sequence
<220> FEATURE:
<223> OTHER INFORMATION: oligo

<400> SEQUENCE: 7
ctctcccctt gccctaggc                                                19
```

```
<210> SEQ ID NO 8
<211> LENGTH: 19
<212> TYPE: DNA
<213> ORGANISM: Artificial Sequence
<220> FEATURE:
<223> OTHER INFORMATION: oligo

<400> SEQUENCE: 8
cctaggctct ggccgttgc                                                       19

<210> SEQ ID NO 9
<211> LENGTH: 23
<212> TYPE: DNA
<213> ORGANISM: Artificial Sequence
<220> FEATURE:
<223> OTHER INFORMATION: oligo

<400> SEQUENCE: 9
atatccgccg ctgttaccct atc                                                  23

<210> SEQ ID NO 10
<211> LENGTH: 23
<212> TYPE: DNA
<213> ORGANISM: Artificial Sequence
<220> FEATURE:
<223> OTHER INFORMATION: oligo

<400> SEQUENCE: 10
atatccgccg ctgttaccct atc                                                  23

<210> SEQ ID NO 11
<211> LENGTH: 26
<212> TYPE: DNA
<213> ORGANISM: Artificial Sequence
<220> FEATURE:
<223> OTHER INFORMATION: oligo

<400> SEQUENCE: 11
atatccgccg ctgttaccct atccaa                                               26

<210> SEQ ID NO 12
<211> LENGTH: 30
<212> TYPE: DNA
<213> ORGANISM: Artificial Sequence
<220> FEATURE:
<223> OTHER INFORMATION: oligo

<400> SEQUENCE: 12
catggagctg taggagtcta aattggggac                                           30

<210> SEQ ID NO 13
<211> LENGTH: 33
<212> TYPE: DNA
<213> ORGANISM: Artificial Sequence
<220> FEATURE:
<223> OTHER INFORMATION: oligo

<400> SEQUENCE: 13
tagcatggag ctgtaggagt ctaaattggg gac                                       33

<210> SEQ ID NO 14
<211> LENGTH: 37
<212> TYPE: DNA
<213> ORGANISM: Artificial Sequence
<220> FEATURE:
<223> OTHER INFORMATION: oligo
```

```
<400> SEQUENCE: 14
tagcatggag ctgtaggagt ctaaattggg gacgcag                    37
```

HAV DETECTION

CROSS-REFERENCE TO RELATED APPLICATIONS

This application claims priority to U.S. Provisional Application Ser. No. 61/736,686, filed on Dec. 13, 2012.

FIELD OF THE INVENTION

The invention relates to methods for the detection of HAV using oligonucleotides, use and reaction mixtures of oligonucleotides for the detection of HAV, and a kit comprising oligonucleotides for the detection of HAV.

BACKGROUND OF THE INVENTION

HAV (Hepatitis A Virus) is an RNA virus classified as hepatovirus which can cause Hepatitis, an acute infection of the liver. HAV is usually spread by a fecal route, transmitted person-to-person by ingestion of contaminated food or water or through direct contact with an infectious person.

Hepatitis A has an incubation period of about four weeks. The virus replicates in the liver. Relatively large quantities of virus are shed in the feces during the incubation period before the onset of clinical symptoms, and a brief viremia occurs. The severity of illness ranges from the asymptomatic to anicteric or icteric hepatitis. The virus is non-cytopathic when grown in cell culture. Its pathogenicity in vivo, which involves necrosis of parenchymal cells and histiocytic periportal inflammation, may be mediated by cellular immune responses. By the time of onset of symptoms, excretion of virus in the feces has declined and may have ceased and anti-HAV IgM increases in titer. Anti-HAV IgG may be detected one to two weeks later and persists for years. The HAV genome comprises about 7,500 nucleotides (nt) of positive sense RNA which is polyadenylated at the 3' end and has a polypeptide (VPg) attached to the 5' end. A single, large open reading frame (ORF) occupies most of the genome and encodes a polyprotein with a theoretical molecular mass of $M_r$ 252,000. The HAV polyprotein is processed to yield the structural (located at the amino-terminal end) and non-structural viral polypeptides. Many of the features of replication of the picornaviruses have been deduced from studies of prototype enteroviruses and rhinoviruses, in particular poliovirus type 1.

Hepatitis A virus enters the body by ingestion and intestinal infection. The virus then spreads, probably by the bloodstream, to the liver, a target organ. Large numbers of virus particles are detectable in feces during the incubation period, beginning as early as 10-14 days after exposure and continuing, in general, until peak elevation of serum aminotransferases. Virus is also detected in feces early in the acute phase of illness, but relatively infrequently after the onset of clinical jaundice. Interestingly, antibody to hepatitis A virus that persists is also detectable late in the incubation period, coinciding approximately with the onset of biochemical evidence of liver damage. Hepatitis A antigen has been localized by immunofluorescence in the cytoplasm of hepatocytes after experimental transmission to chimpanzees. The antigen has not been found in any tissue other than the liver following intravenous inoculation.

Various serologic tests are available for hepatitis A, including immune electron microscopy, complement-fixation, immune adherence hemagglutination, radioimmunoassay, and enzyme immunoassay. Immune adherence hemagglutination, which had been widely used, is moderately specific and sensitive. Several methods of radioimmunoassay have been described; of these, a solid-phase type of assay is particularly convenient, very sensitive, and specific. Very sensitive enzyme immunoassay techniques are used widely. Only one serotype of hepatitis A virus has been identified in volunteers infected experimentally with the MS-1 strain of hepatitis A, in patients from different outbreaks of hepatitis in different geographic regions, and in random cases of hepatitis A. Isolation of virus in tissue culture requires prolonged adaptation and it is, therefore, not suitable for diagnosis.

Molecular biology techniques, for example those based on reverse transcription of viral RNA and its amplification by PCR, allow detection of very small amounts of viral RNA from any kind of clinical or environmental sample. HAV infection can be detected by nucleic acid testing methods as provided in the present invention.

BRIEF SUMMARY OF THE INVENTION

The present invention provides methods of detecting HAV in a biological sample, comprising amplifying a target nucleic acid comprising the nucleic acid sequence of HAV in a reaction mixture. The reaction mixture may comprise a biological sample which may contain the target nucleic acid and at least a first and a second primer, wherein the nucleic acid sequence of the first primer is selected from SEQ ID NOS: 5-8 and the nucleic acid sequence of the second primer is selected from SEQ ID NOS: 10-11. The amplification generates an amplified target nucleic acid which can be detected.

Further the present invention provides methods wherein the amplified target nucleic acid is detected either during or following the amplification. The methods may also comprise reaction mixtures further comprising a probe for detecting the amplified target nucleic acid. The nucleic acid sequence of the probe is selected from SEQ ID NOS: 13-14.

The methods also provide wherein a second target nucleic acid is detected in parallel with HAV in a separate vial which does not contain HAV, under the same cycling conditions and in a reaction mixture comprising the same proportion of amplification reagents.

The present invention also provides reaction mixtures comprising a first primer and a second primer, wherein the nucleic acid sequence of the first primer is selected from SEQ ID NOS: 5-8 and the nucleic acid sequence of the second primer is selected from SEQ ID NOS: 10-11. Further the reaction mixtures may contain a probe, wherein the nucleic acid sequence of the probe is selected from SEQ ID NOS: 13-14. The invention also provides kits comprising a polymerase, nucleotides and a first primer and a second primer, and optionally providing a probe. Further for example the nucleic acid sequence of the first primer can be SEQ ID NO: 7, and the nucleic acid sequence of the second primer can be SEQ ID NO: 11, and the nucleic acid sequence of the probe can be SEQ ID NO:14.

The present invention further provides methods further comprising amplifying and detecting a second target nucleic acid in the biological sample in the reaction mixture. For example the second target nucleic acid may be parvovirus B19, or may be another virus or bacteria or microbe or other sequence of interest including a genetic target or a control target.

DETAILED DESCRIPTION OF THE INVENTION

Methods of detecting HAV in a biological sample are disclosed, comprising amplifying a target nucleic acid comprising the sequence of HAV in a reaction mixture. The reaction mixture comprises a biological sample which may contain the target nucleic acid, and a set of oligonucleotides or a pair of primers. The nucleic acid sequence of the first primer may be selected from SEQ ID NOS: 5 to 8 and the nucleic acid sequence of the second primer may be selected from SEQ ID NOS: 10 to 11. The amplifying step may generate an amplified target nucleic acid. The method further comprises the step of detecting the amplified nucleic acid.

The term "biological sample" relates to material that can be subjected to a diagnostic assay targeting nucleic acids and is usually derived from a biological source. In some embodiments, said biological sample is derived from a human and is a body liquid. In one embodiment of the invention, the biological sample is human blood, urine, sputum, sweat, swab, pipettable stool, or spinal fluid. The biological sample may also be a tissue from which target nucleic acids may be extracted.

The term "amplifying" as used herein generally refers to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to: standard PCR, long PCR, real time PCR, hot start PCR, qPCR, RT (reverse transcription) PCR and Isothermal Amplification. Other amplification reactions comprise, among others, the Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification. The process of amplifying creates an amplification product, termed for example and amplicon or an amplified nucleic acid or an amplified target nucleic acid.

For example a method of nucleic acid amplification is the Polymerase Chain Reaction (PCR) which is disclosed, among other references, in U.S. Pat. Nos. 4,683,202, 4,683,195, 4,800,159, and 4,965,188. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer can be single-stranded for maximum efficiency in amplification, but the primer can be double-stranded. Double-stranded primers are first denatured, i.e., treated to separate the strands. One method of denaturing double stranded nucleic acids is by heating.

A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have e.g. been isolated from *Thermus flavus, T. ruber, T. thermophilus, T. aquaticus, T. lacteus, T. rubens, Bacillus stearothermophilus,* and *Methanothermus fervidus*. Another exemplary polymerase is Z05. Polymerases may also be modified from their original state, for example to perform additional functions and/or have improved functionality. For example Z05D is a modified Z05 polymerase, for example as described in US 2009/0148891. A "polymerase with reverse transcriptase activity" is a nucleic acid polymerase capable of synthesizing DNA based on an RNA template. It is also capable of the formation of a double-stranded DNA once the RNA has been reverse transcribed into a single strand cDNA. In an embodiment of the invention, the polymerase is thermostable. Polymerases that are not thermostable also can be employed in PCR assays provided the enzyme is replenished. Multiple polymerases can also be blended in one reaction mixture to provide multiple functions.

A "target nucleic acid" is a polymeric compound of nucleotides as known to the expert skilled in the art. "Target nucleic acid" is used herein to denote a nucleic acid in a sample which should be analyzed, i.e. the presence, non-presence and/or amount thereof in a sample should be determined. The target nucleic acid may be a genomic sequence, e.g. part of a specific gene, or RNA or DNA. In other embodiments, the target nucleic acid may be viral or microbial. In a specific embodiment, the target nucleic acids may be HAV or Parvovirus B19. The target nucleic acid may also be a control target.

The term "reaction mixture" relates to the medium in which the amplification reaction occurs. The medium may be a liquid, a suspension of particles or a liquid in connection with a solid phase. The medium comprises salts, reagents such as dNTPs, enzymes and oligonucleotides that are necessary to obtain amplification of the target nucleic acids and a sample which may comprise the target nucleic acid.

In one embodiment, the reaction mixture additionally comprises a nucleic acid probe for detection of the amplified target nucleic acid. In one specific embodiment, for example, the nucleic acid sequence of the probe can be SEQ ID NO: 14.

The term "which may contain the target nucleic acid" means that not only samples which contain or are, for some reason, suspected to contain the target nucleic acid are tested, but rather, samples are tested which may contain the target nucleic acid, even if eventually, they do not contain the target nucleic acid.

The terms "primer" and "probe" as used herein relate to oligonucleotides. In the context of this invention, the term "oligonucleotide" refers to components formed from a plurality of nucleotides as their monomeric units. The term "oligonucleotide" also includes modified oligonucleotides, i.e. the primer and/or the probe comprise a modified nucleotide or a non-nucleotide compound also termed a nucleotide analog. The term "primers" further relates to such oligonucleotides which are used in amplification reactions and anneal to a target sequence. The term "probe" further relates to oligonucleotides which are hybridized to a target nucleic acid or an amplicon for the purpose of either qualitative or quantitative detection. In the case of a probe, modifications may include dyes, such as FAM, HEX, JA270, CY5, CY5.5 etc. and/or Quencher molecules. Dye molecules may be coupled to linkers. Such dyes may, however, also be present in primers. Other exemplary modifications include a phosphate group at the 3' end. Common modifications of primers include modification of the 3' nucleotides to prevent unspecific amplification products such as primer dimers. Such modifications are well known in the art and include, as non-limiting examples, t-Butyl benzyl-dA or -Butyl benzyl-dC. Such modifications are also included in the term "primer".

A pair of primers refers to a forward and a reverse primer which, together, can produce an amplicon from a target nucleic acid to which they anneal if subjected to conditions that allow such a production of an amplicon. More than 2 primers may be found in a reaction mixture. A set of oligonucleotides for amplifying may comprise multiple primers and 1 or 2 or more probes.

The term "detecting" relates to the measurement of a signal which is produced upon amplification. Measurement may be qualitative or quantitative. Suitable nucleic acid detection methods are known to the expert in the field and are described in standard textbooks as Sambrook J. et al., Molecular Cloning: A Laboratory Manual, Cold Spring Harbor Laboratory Press, Cold Spring Harbor, N.Y., 1989 and Ausubel F. et al.: Current Protocols in Molecular Biology 1987, J. Wiley and Sons, NY. There may be also further purification steps before the nucleic acid detection step is carried out as e.g. a precipitation step. The detection methods may include but are not limited to the binding or intercalating of specific dyes as ethidium bromide which intercalates into the double-stranded DNA and changes its fluorescence thereafter. The purified nucleic acid may also be separated by electrophoretic methods optionally after a restriction digest and visualized thereafter. There are also probe-based assays which exploit the oligonucleotide hybridization to specific sequences and subsequent detection of the hybrid.

The amplified target nucleic acids can be detected during or after the amplification reaction in order to evaluate the result of the analysis. One method for detection in real time is the use of a nucleic acid probe or multiple probes. Other real time methods are well known in the art and include for example the use of DNA binding dyes such as SYBR green or ethidium bromide.

By using commercially available real-time PCR instrumentation (e.g., LightCycler® or TaqMan® systems), PCR amplification and detection of the amplification product can be combined in a single closed container with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory. However, other detection methods known to the skilled person may also be used.

By using an internal control nucleic acid according to the methods of the invention, sample-specific, but also sample-unspecific inhibitory effects possibly interfering with the amplification and detection reactions (target region-independent inhibition) are leveled resulting in more accurate titers. "Internal" means that the control nucleic acid is amplified, detected and quantified within the same reaction mixture as the target nucleic acid instead of in a separate experiment. For example the present invention provides for the addition of control oligonucleotides—forward primer, reverse primers and a probe—to the reaction mixtures.

"Limit of detection" or "LOD" means the lowest detectable amount or concentration of a nucleic acid in a sample with a predefined hit rate. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is copy of the respective nucleic acid. IU/ml stands for "International units/ml", referring to the WHO standard.

A widely used method for calculating an LOD is "Probit Analysis", which is a method of analyzing the relationship between a stimulus (dose) and the quantal (all or nothing) response. In a typical quantal response experiment, groups of animals are given different doses of a drug. The percent dying at each dose level is recorded. These data may then be analyzed using Probit Analysis. The Probit Model assumes that the percent response is related to the log dose as the cumulative normal distribution. That is, the log doses may be used as variables to read the percent dying from the cumulative normal. Using the normal distribution, rather than other probability distributions, influences the predicted response rate at the high and low ends of possible doses, but has little influence near the middle.

The "Probit Analysis" can be applied at distinct "hit rates". As known in the art, "hit rate" is commonly expressed in percent [%] and indicates the percentage of positive results at a specific concentration of an analyte. Thus for example, an LOD can be determined at 95% hit rate, which means that the LOD is calculated for a setting in which 95% of the valid results are positive.

In one embodiment, nucleic acids present in the biological sample are enriched prior to reverse transcription and amplification.

The term "enriched" as used herein relates to any method of treating a sample comprising a target nucleic acid that allows to separate the target nucleic acid from at least a part of other material present in the sample. "Enrichment" can, thus, be understood as a production of a higher amount of target nucleic acid over other material.

There are several methods for the enrichment of nucleic acids:

Sequence-dependent or biospecific methods as e.g.:
affinity chromatography
hybridization to immobilized probes
Sequence-independent or physico-chemical methods as e.g.:
liquid-liquid extraction with e.g. phenol-chloroform
precipitation with e.g. pure ethanol
extraction with filter paper
extraction with micelle-forming agents as cetyl-trimethyl-ammonium-bromide
binding to immobilized, intercalating dyes, e.g. acridine derivatives
adsorption to silica gel or diatomic earths
adsorption to magnetic glass particles (MGP) or organo-silane particles under chaotropic conditions An exemplary method for enriching target nucleic acid is enrichment using Puregene-Kits commercially available from Qiagen (e.g order number 158389).

Another aspect of the invention is the process described supra, wherein enrichment is preceded by releasing nucleic acids from their cellular and/or viral environment by lysing cells and/or viral capsids potentially present in the plurality of different fluid samples.

To release the contents of cells or viral particles, they may be treated with enzymes or with chemicals to dissolve, degrade or denature the cellular walls or viral particles. This process is commonly referred to as lysis. The resulting solution containing such lysed material is referred to as lysate.

In one embodiment, the amplification and detection steps of the method hereinbefore described are preceded by the following steps: A plurality of vessels comprising different types of fluid samples is provided. A solid support material is combined together with the plurality of different types of fluid samples in vessels for a period of time and under conditions sufficient to permit nucleic acids comprising the target nucleic acids to be immobilized on the solid support material. The solid support material is then isolated from the other material present in the fluid samples in a separation station, and the nucleic acids are purified in a separation station by separating the fluid sample from the solid support material and washing the solid support material one or more times with a wash buffer. The physical conditions and the period of time of the combining of the solid support material and the plurality of different types of fluid samples are identical for any one of the plurality of different types of fluid samples.

In one embodiment of the invention, the lysis buffer in the process described above comprises one or more components selected from the group of
a chaotropic agent
a buffer substance
an alcohol
a reducing agent.

Chaotropic agents, which generally disturb the ordered structure of water molecules in solution and non-covalent binding forces in and between molecules, can make several contributions to the procedure of sample preparation. In particular, but not only, they can be applied as RNase inhibitors by disturbing the nuclease's tertiary structure. Usually, no further RNase inhibitor has to be applied to the lysis buffer. Besides, chaotropic agents contribute to the disruption of biological membranes, such as plasma membranes or the membranes of cell organelles if present. Also, they can play a significant role in the adhesive binding of nucleic acids to surfaces like glass (see infra). Chaotropic agents in the context of the invention are guanidinium salts like guanidinium thiocyanate or guanidinium hydrochloride or guanidinium chloride or guanidinium isothiocyanate, urea, perchlorates such as e.g. potassium perchlorate, other thiocyanates or potassium iodide. However, other chaotropic agents can also be used within the scope of the invention.

In an embodiment, the detection of HAV may be performed simultaneously in the same reaction mixture with the detection of Parvovirus B19. Oligonucleotide sequences for detection of Parvovirus B19 are disclosed for example in US2007-0281294. In an embodiment, the amplifying and detecting a second target nucleic acid may be performed in the same reaction mixture along with the amplifying and detecting of HAV. In an embodiment, HAV and Parvovirus B19 are amplified and detected in the same reaction mixture. In an embodiment, a kit is provided comprising sets of oligonucleotides for amplifying HAV and a second target. In an embodiment, for example the second target is Parvovirus B19. In another embodiment the kit further comprises sets of oligonucleotides to additional targets.

In an embodiment, the detection of the amplified nucleic acid may occur during amplification, for example using real-time PCR techniques. In another embodiment the detection of the amplified nucleic acid may occur after the completion of the amplification.

In another embodiment of the invention, a second target nucleic acid is detected in parallel with HAV in a separate vial which does not contain HAV, under the same cycling conditions and in a reaction mixture comprising the same proportion of amplification reagents. The term "in parallel" means that HAV and the second target nucleic acid are subjected to the method in separate vials, but at the same time and under the same conditions.

The invention also provides a set of oligonucleotide or a pair of primers comprising a first and a second primer, wherein the nucleic acid sequence of the first primer comprises one of SEQ ID NOS: 5-8 and the nucleic acid sequence of the second primer comprises one of SEQ ID NOS: 10-11. This primer pair may be used in a hybridization reaction with a complementary nucleic acid. Furthermore, the primer pair and the probe herein described may be used for detecting HAV.

The invention further provides a set of oligonucleotides comprising a first and a second primer, wherein the nucleic acid sequence of the first primer comprises one of SEQ ID NOS: 5-8 and the nucleic acid sequence of the second primer comprises one of SEQ ID NOS: 10-11, and a probe, wherein the nucleic acid sequence of the probe comprises one of SEQ ID NOS: 13-14.

The invention also provides kits comprising a polymerase, nucleotides and oligonucleotides as described herein. In one embodiment, the kit additionally comprises a probe, wherein the nucleic acid sequence of said probe comprises one of SEQ ID NOS: 13-14. The kit may be used for the detection of HAV. Further embodiments of kit components are as disclosed herein.

In one embodiment, for the method, primer pairs, oligonucleotide set and kit described herein, the forward primer is SEQ ID NO: 2, and the reverse primer is SEQ ID NO: 10. In one embodiment the probe is SEQ ID NOS: 13 or 14. In one embodiment, for the method, primer pairs, oligonucleotide set and kit described herein, the forward primer is SEQ ID NO: 2, and the reverse primer is SEQ ID NO: 11. In one embodiment the probe is SEQ ID NOS: 13 or 14. In one embodiment, for the method, primer pairs, oligonucleotide set and kit described herein, the forward primer is SEQ ID NO:3, and the reverse primer is SEQ ID NO: 10. In one embodiment the probe is SEQ ID NOS: 13 or 14. In one embodiment, for the method, primer pairs, oligonucleotide set and kit described herein, the forward primer is SEQ ID NO: 3, and the reverse primer is SEQ ID NO: 11. In one embodiment the probe is SEQ ID NOS: 13 or 14. In one embodiment, for the method, primer pairs, oligonucleotide set and kit described herein, the forward primer is SEQ ID NO: 4, and the reverse primer is SEQ ID NO: 10. In one embodiment the probe is SEQ ID NOS: 13 or 14.

In one embodiment, for the method, primer pairs, oligonucleotide set and kit described herein, the forward primer is SEQ ID NO: 4, and the reverse primer is SEQ ID NO: 11. In one embodiment the probe is SEQ ID NOS: 13 or 14. In one embodiment, for the method, primer pairs, oligonucleotide set and kit described herein, the forward primer is SEQ ID NO: 5, and the reverse primer is SEQ ID NO: 10. In one embodiment the probe is SEQ ID NOS: 13 or 14. In one embodiment, for the method, primer pairs, oligonucleotide set and kit described herein, the forward primer is SEQ ID NO: 5, and the reverse primer is SEQ ID NO: 11. In one embodiment the probe is SEQ ID NOS: 13 or 14. In one embodiment, for the method, primer pairs, oligonucleotide set and kit described herein, the forward primer is SEQ ID NO: 6, and the reverse primer is SEQ ID NO: 10. In one embodiment the probe is SEQ ID NOS: 13 or 14. In one embodiment, for the method, primer pairs, oligonucleotide set and kit described herein, the forward primer is SEQ ID NO: 6, and the reverse primer is SEQ ID NO: 11. In one embodiment the probe is SEQ ID NOS: 13 or 14.

In one embodiment, for the method, primer pairs, oligonucleotide set and kit described herein, the forward primer is SEQ ID NO:7, and the reverse primer is SEQ ID NO: 10. In one embodiment the probe is SEQ ID NOS: 13 or 14. In one embodiment, for the method, primer pairs, oligonucleotide set and kit described herein, the forward primer is SEQ ID NO: 7, and the reverse primer is SEQ ID NO: 11. In one embodiment the probe is SEQ ID NOS: 13 or 14. In one embodiment, for the method, primer pairs, oligonucleotide set and kit described herein, the forward primer is SEQ ID NO: 8, and the reverse primer is SEQ ID NO: 10. In one embodiment the probe is SEQ ID NOS: 13 or 14. In one embodiment, for the method, primer pairs, oligonucleotide set and kit described herein, the forward primer is SEQ ID NO: 8, and the reverse primer is SEQ ID NO: 11. In one embodiment the probe is SEQ ID NOS: 13 or 14.

In the examples described below, further as provided in Table 2, an increased sensitivity with R2-HAV oligonucleotide set was observed for SEQ ID NO: 7, 11, compared to the R2 HAVref oligonucleotide set. In one embodiment, SEQ ID NOS: 7, 11, and 14 are used.

EXAMPLES

The following examples are offered to illustrate, but not to limit the claimed invention.

Comparison of Two Oligonucleotide Sets

A side-by-side limit of detection (LOD) study for HAV is conducted comparing two oligonucleotide sets.

Reagent MMx R2-HAV comprises oligonucleotides comprising the nucleic acid sequence of one of SEQ ID NOS: 5-8, one of SEQ ID NOS: 10-11, and one of SEQ ID NOS: 13-14;

Reagent MMx R2-HAVref (the REFERENCE set) comprises oligonucleotides comprising the nucleic acid sequence of SEQ ID NO: 1, SEQ ID NO: 9 and SEQ ID NO: 12.

The HAV-positive specimens used to create the test level nodes are additionally spiked with Parvovirus B19 as viral background level. The specimen dilution panels are prepared as shown in Table 1.

TABLE 1

Specimen dilution panels

| Node | Parvovirus B19 Concentration in IU/mL | HAV Concentration in IU/mL | Number of replicates per node and oligonucleotide set |
|---|---|---|---|
| 1 | 500 | 6.000 | 21 |
| 2 | 500 | 3.000 | 21 |
| 3 | 500 | 1.500 | 21 |
| 4 | 500 | 0.750 | 21 |
| 5 | 500 | 0.375 | 21 |
| 6 | 500 | 0.188 | 21 |
| 7 | 0 | 0 | 18 |

For each specimen replicate of node 1 to 7, 850 µL samples are pipetted manually into deep-well plates (process plates). The process plates are subjected to a sample preparation for nucleic acid extraction on a semi-automated functional module (Roche), using a generic sample preparation process as described in US-2012-0045751.

During the final sample preparation step (eluate cool down) the Master Mixes (MMx), containing amplification reagents MMx R1 and MMx R2 (R2-HAV or R2-HAVref), are added manually to each well of a micro-well plate (Amplification-Detection-Plate). Amplification reagents R1 and R2 are further defined below. The eluates (containing the isolated nucleic acids) are then transferred by the instrument from the process-plate to the micro-well plate and mixed with the MMx. The micro-well plates are then sealed automatically and transferred manually into the stand-alone analytical cycler for amplification and detection. The amplification and detection (Real Time PCR) are carried out simultaneously and under identical conditions for both Master Mixes using a suitable PCR profile.

Amplification and Detection

For amplification, the two reagents MMx R1 and MMx R2 (R2-HAV or R2-HAVref) are combined and mixed with the isolated nucleic acids to a total reaction volume of 50 µL in the following manner:

10 µL MMx R1 reagent (3.3 mM MnOAc, pH 6.1, and 0.02% Sodium azide pH 7.0), 15 µL MMx R2 reagent (R2-HAV or R2-HAVref) and 25 µL isolated nucleic acids are combined to result in a reaction solution.

The formulations of MMx R2-HAV and MMx R2-HAVref only differ in their HAV oligonucleotide composition. In this example, MMx R2-HAV comprises oligonucleotide set 1 (SEQ ID NOS: 7, 11 and 14), MMx R2-HAVref comprises oligonucleotide set 2 (SEQ ID NOS: 1, 9 and 12). Both sets are tested with the same primer/probe concentrations.

For the present examples, the reaction mixture with oligo set 1 comprises 0.03% Sodium azide pH 7.0, 5.4% DMSO, 120 mM KOAc pH 7.0, 3% Glycerol, 0.02% Tween 20, 60 mM Tricine pH 8.0, 0.2222 uM aptamer, 10 U UNG, 0.4 mM dGTP, 0.4 mM dATP, 0.4 mM dCTP, 0.8 mM dUTP, 45 U Z05D polymerase, 0.35 uM HAV fwd primer, 0.15 uM HAV sense probe, 0.35 uM HAV rev primer; 0.3 uM internal control fwd primer, 0.3 uM internal control rev primer, 0.15 uM internal control probe. The reaction mixture for HAVref comprises the same concentrations of oligonucleotides as the HAV reaction mixture.

Data Analysis

The raw data files of the Analytical Cycler are analysed using automated software. LOD is determined using a Probit-Dose Response Tool. The calculated Probit data (95%) are listed in Table 2.

TABLE 2

Probit data (95%) for MMx R2-HAV and MMx R2-HAVref

|  | prob | Concentration IU/ml |
|---|---|---|
| R2-HAV | 0.95 | 1.27 |
| R2-HAVref | 0.95 | 1.97 |

This Probit data shows that the R2-HAV oligonucleotide set results in increased sensitivity (1.27) over the R2-HAVref oligonucleotide set (1.97).

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method of detecting Hepatitis A Virus (HAV) in a biological sample, comprising:
   (a) amplifying a target nucleic acid comprising the nucleic acid sequence of HAV in a reaction mixture, the reaction mixture comprising:
      (i) the biological sample which may contain the target nucleic acid, wherein the target nucleic acid is not isolated or separated from the biological sample;
      (ii) a forward primer consisting of SEQ ID NO: 7 and a reverse primer consisting of SEQ ID NO: 11, wherein the forward primer and the reverse primer contact the target nucleic acid in the biological sample and initiate extension by a polymerase, thereby amplifying the target nucleic acid, if the target nucleic acid is present in the biological sample, wherein the amplifying generates an amplified target nucleic acid, and
      (iii) a probe consisting of SEQ ID NO: 14 for detecting the amplified target nucleic acid; and
   (b) detecting the amplified target nucleic acid.

2. The method of claim 1, wherein the amplified target nucleic acid is detected either during or following step (a).

3. The method of claim 1, wherein a second target nucleic acid is detected in parallel with HAV in a separate vial, which does not contain HAV, under the same cycling conditions and in a reaction mixture comprising the same proportion of amplification reagents.

4. The method of claim 1, further comprising amplifying and detecting a second target nucleic acid in the biological sample in the reaction mixture.

5. The method of claim 4, wherein the second target nucleic acid is parvovirus B19.

* * * * *